(12) United States Patent
Liu et al.

(10) Patent No.: US 9,597,293 B2
(45) Date of Patent: Mar. 21, 2017

(54) SOLID DOSAGE FORMS COMPRISING AN ENTERIC COATING WITH ACCELERATED DRUG RELEASE

(75) Inventors: Fang Liu, London (GB); Abdul W. Basit, Harrow Middlesex (GB); Rosario Lizio, Dieburg (DE); Hans-Ulrich Petereit, Darmstadt (DE); Christian Meier, Darmstadt (DE); Michael Damm, Roedermark (DE)

(73) Assignee: EVONIK RÖHM GmbH, Darmstadt (DE)

( * ) Notice: Subject to any disclaimer, the term of this patent is extended or adjusted under 35 U.S.C. 154(b) by 1668 days.

(21) Appl. No.: 12/598,138

(22) PCT Filed: May 7, 2007

(86) PCT No.: PCT/EP2007/054398
§ 371 (c)(1),
(2), (4) Date: Oct. 29, 2009

(87) PCT Pub. No.: WO2008/135090
PCT Pub. Date: Nov. 13, 2008

(65) Prior Publication Data
US 2010/0129446 A1 May 27, 2010

(51) Int. Cl.
| | | |
|---|---|---|
| *A61K 9/32* | (2006.01) | |
| *A61K 47/12* | (2006.01) | |
| *A61K 47/32* | (2006.01) | |
| *A61K 47/34* | (2006.01) | |
| *A61K 47/38* | (2006.01) | |
| *A61K 9/50* | (2006.01) | |

(52) U.S. Cl.
CPC .......... *A61K 9/5073* (2013.01); *A61K 9/5026* (2013.01)

(58) Field of Classification Search
CPC .................. A61K 9/5073; A61K 9/5026
See application file for complete search history.

(56) References Cited

U.S. PATENT DOCUMENTS

| | | | |
|---|---|---|---|
| 4,520,172 A * | 5/1985 | Lehmann et al. | 525/369 |
| 6,013,281 A | 1/2000 | Lundberg et al. | |
| 6,312,728 B1 * | 11/2001 | Beiman et al. | 424/490 |
| 6,623,759 B2 * | 9/2003 | Heese et al. | 424/480 |
| 7,932,258 B2 * | 4/2011 | Petereit et al. | 514/263.3 |

| | | |
|---|---|---|
| 2002/0054913 A1 | 5/2002 | Heese et al. |
| 2002/0098235 A1 | 7/2002 | Dittmar et al. |
| 2003/0152627 A1 | 8/2003 | Beckert et al. |
| 2004/0028737 A1 | 2/2004 | Deshpande et al. |
| 2005/0287211 A1 | 12/2005 | Yoshida et al. |
| 2008/0026051 A1 | 1/2008 | Lizio et al. |
| 2008/0044470 A1 | 2/2008 | Petereit et al. |
| 2008/0200482 A1 | 8/2008 | Petereit et al. |
| 2009/0041842 A1 | 2/2009 | Lizio et al. |
| 2010/0247639 A1 | 9/2010 | Ravishankar et al. |

FOREIGN PATENT DOCUMENTS

| | | |
|---|---|---|
| CA | 2 444 814 A1 | 5/2002 |
| DE | 10 2005 032 806 | 1/2007 |
| EP | 0 453 001 A1 | 10/1991 |
| JP | 58-135807 | 8/1983 |
| JP | 2000-514051 | 10/2000 |
| JP | 2003-524592 | 8/2003 |
| WO | WO 03/045356 A1 | 6/2003 |
| WO | WO 2006/042277 A2 | 4/2006 |
| WO | WO 2006/087027 A1 | 8/2006 |
| WO | WO 2007/006353 A2 | 1/2007 |

OTHER PUBLICATIONS

Basit, Abdul W. et al., "The use of Formulation Technology to Assess Regional Gastrointestinal Drug Absorption in Humans", European Journal of Pharmaceutical Sciences, vol. 21, No. 2-3, pp. 179-189 (Feb. 1, 2004) XP002454848.
Office Action mailed May 14, 2015, in co-pending U.S. Appl. No. 13/603,984.
Examination Report issued Apr. 16, 2015, in European Patent Application No. 07 728 851.2-1460, filed May 7, 2007.
Office Action issued Sep. 3, 2013, in Korean Patent Application No. 20097023249, filed May 7, 2007 (w/English-language Translation).
Office Action mailed Oct. 4, 2013, in co-pending U.S. Appl. No. 13/603,984.
Office Action issued Aug. 7, 2014, in Israeli Patent Application No. 201557.

* cited by examiner

*Primary Examiner* — Kevin S Orwig
*Assistant Examiner* — Lisbeth C Robinson
(74) *Attorney, Agent, or Firm* — Oblon, McClelland, Maier & Neustadt, L.L.P.

(57) ABSTRACT

The present invention provides a solid dosage form including an inner coating located between a core containing a pharmaceutically active ingredient and an outer enteric coating; wherein the inner coating includes a partially neutralized anionic polymeric material, and at least a carboxylic acid having 2 to 16 carbon atoms the salts thereof or mixtures of the acid and its salt; wherein the outer coating includes an anionic polymeric material which is less or not at all neutralized than the material of the inner coating.

11 Claims, No Drawings

SOLID DOSAGE FORMS COMPRISING AN ENTERIC COATING WITH ACCELERATED DRUG RELEASE

CROSS-REFERENCE TO RELATED APPLICATIONS

This application is a National Stage of PCT/EP07/54398 filed May 7, 2007.

The invention refers to Solid dosage forms comprising an enteric coating with accelerated drug release.

BACKGROUND OF THE INVENTION

Enteric coated products are designed to remain intact in the stomach and then to release the active substance in the intestine. Enteric coating can be applied to solid dosage forms, such as granules, pellets, capsules, or tablets. The purpose of enteric coating is to protect the stomach from irritating active compounds such as aspirin, or to improve drug bioavailability by preventing degradation of acid or gastric enzyme labile drugs. Enteric coatings have been developed for more than one century. The first real enteric coating was believed to use keratin by Unna in 1884. Some of the earlier coatings depended on the enzymatic breakdown or emulsifying effect of the films in the small intestine, such as enteric films based on stearic acid.

Almost all the currently used enteric materials are synthetic or modified natural polymers containing ionizable carboxylic groups. In the low pH environment of the stomach, the carboxylic groups remain un-ionized, and the polymer coatings remain insoluble. In the intestine, the pH increases to 5 and above, allowing the carboxylic groups on the polymeric coating materials to ionize, and the polymer coatings to disintegrate or dissolve, releasing their contents. Based on the purpose of an enteric coating, an ideal enteric coating should possess the following properties: 1. Must resist disintegration or dissolution in the stomach for as long as the dosage form remains there; 2. Must dissolve or disintegrate rapidly in the small intestine; 3. Must be physically and chemically stable during storage; 4. Must be non-toxic; 5. Must be easily applied as a coating; 6. Must be economical.

Table 1 shows some commonly used enteric-coating materials for upper small intestinal drug release.

|  | Abbreviation | Type | Solubility |
|---|---|---|---|
| Cellulose acetate phthalate | CAP |  | Soluble in intestinal fluid from pH 6.0 |
| Polyvinyl acetate phthalate | PVAP |  | Soluble in intestinal fluid from pH 5.5 |
| Hydroxypropyl methylcellulose phthalate | HPMCP | HP-50 | Soluble in intestinal fluid from pH 5.0 |
|  |  | HP-55 | Soluble in intestinal fluid from pH 5.5 |
| Poly-methacrylates |  | Eudragit® L 100-55 | Soluble in intestinal fluid from pH 5.5 |
|  |  | Eudragit® L 30 D-55 | Soluble in intestinal fluid from pH 5.5 |
|  |  | Eudragit® L 100 | Soluble in intestinal fluid from pH 6.0 |

It is commonly believed that enteric-coated dosage forms, coated with low dissolution threshold pH polymers such as polyvinyl acetate phthalate, cellulose acetate phthalate or Eudragit® L 100-55, rapidly disintegrate on entry into the small intestine, however, this is not the case.

There is indeed a discrepancy between in vitro and in vivo performance of enteric coatings. For those enteric-coated dosage forms, coated with low dissolution threshold pH polymers, in vitro disintegration always occurs rapidly within few minutes in simulated intestinal pH. In addition, the in vitro dissolution studies normally require that when the enteric-coated products were placed in pH 6.8 buffer, greater than 80% of the drug should be released within 45 min, but in most cases the dissolution time is much shorter than that. However, there is a major discrepancy between in vitro dissolution data and in vivo performance of enteric-coated dosage forms. It can take up to 2 h or 1-2 h or more for the enteric-coated products to disintegrate after gastric emptying.

As small intestinal transit time is of the order of 3-4 hours, disintegration and drug release from such enteric-coated dosage forms will occur in the distal small intestine. In some cases, such delay of drug release from enteric-coated dosage forms could lead to ineffective drug therapy. For example, enzyme supplements constitute the primary approach to treating pancreatic insufficiency of those patients with Cystic Fibrosis (CF). Since patients with CF have lower postprandial duodenal pH compared with healthy people, the enzyme release from conventional enteric-coated dosage forms takes approximately 100 min after gastric emptying. Comparing this release time to the usual small intestine transit time, it appears that as much as half the available contact time between chyme and enzymes could be lost, leading to an insufficient enzyme effect. In addition, for a number of actives, the optimum site of absorption is the upper part of the small intestine. Delayed drug release to distal small intestine could decrease the bioavailability of these drugs in conventional enteric-coated formulations. For instance, the bioavailability of levodopa could be improved by loading high concentrations of the drug at the upper part of the small intestine. An enteric-coated system that releases its drug load promptly on entry into the small intestine would therefore be highly desirable. Such systems would also be of benefit for drugs that are absorbed throughout the small intestine, in terms of rapid onset of action.

The document WO 2007/006353 discloses the use of a partially neutralized anionic (meth)acrylate copolymer comprising radically polymerized units of 25 to 95 percent by weight $C_1$- to $C_4$-alkyl esters of acrylic or of methacrylic acid and 5 to 75 percent by weight of (meth)acrylate monomers having an anionic group, at least 4% of which are neutralized by means of a base, for producing a medicament that is provided with an active substance-containing core and is coated with the partially neutralized, anionic (meth)acrylate copolymer. Said medicament releases at least 30 percent of the active substance contained therein in 30 minutes at a pH at which the active substance is sufficiently soluble and stable and at which the corresponding medicament that is coated with the non-neutralized anionic (meth)acrylate polymer releases less than 10 percent of the active substance contained therein.

The document US 2005/0271778 describes a method for producing pharmaceuticals wherein in the case of gastric resistant solid dosage forms comprising an anionic (meth)acrylate copolymer for the protection of an acid-sensitive active substance contained in the core said polymer is applied to form a gradient in respect to the degree of neutralization of the anionic groups across the thickness of the coating. In the inner region of the coating the anionic groups of the polymer are neutralized to protect the acid labile active substance. The degree of neutralization is decreasing towards the outer region of the coating in order to achieve a gastric resistance of the solid dosage form. In the case of alkali-sensitive solid dosage forms comprising a cationic (meth)acrylate copolymer, for the protection of an alkali-sensitive active substance said cationic polymer is applied to form a gradient in respect to the degree of neutralization of the cationic groups across the thickness of the coating. In the inner region of the coating the cationic groups of the polymer are neutralized to protect the alkali-sensitive active substance. The degree of neutralization of the cationic groups is decreasing towards the outer region of the coating. However, this document does not give any suggestion of how to accelerate the release rate of the active substance.

The document US 2004/0028737 describes enteric coated stable oral pharmaceutical compositions of acid unstable drugs, wherein the enteric coating is a bilayer with a pH gradient across its thickness comprising an inner layer of neutral or near neutral pH 7 to 7.5 and an outer layer of acidic pH 2 to 6. The intention of this document is to achieve stabilization of the acid-sensitive drug. This document does not give any suggestion of how to accelerate the release rate of the active substance.

The document WO 2005/044240 describes a stable formulation for the acid-sensitive lansoprazole, wherein the substrate comprising lansoprazole is coated with a subcoating layer containing an alkaline agent, and an enteric coating on top of this subcoating layer. The document further discloses that as alkaline agent organic basic salts, like sodium stearate, or inorganic basic salts, such as sodium hydrogen carbonate, or other inorganic basic salts which are not water soluble are used. Here again the intention of this state of art is to achieve stabilization of the acid-sensitive drug lansoprazole. This document does not give any suggestion of how to accelerate the release rate of the active substance.

The enteric coated products of this state of art are designed to remain intact in the stomach and then to release the active substance in the upper intestine. The actual observation is that solid dosage forms having the enteric coatings of the state of art do not rapidly disintegrate on entry into the small intestine. Since the small intestinal transit time is of the order of 3 to 4 hours disintegration and drug release from such enteric-coated dosage forms will occur in the distal small intestine. However, this delay of drug release from enteric-coated dosage forms could lead to ineffective drug therapy.

Thus the aim is to provide solid dosage forms with enteric coatings which more rapidly disintegrate on the entry into the small intestine, meaning at an earlier time point when transferred from the stomach having a pH of around 1 to 3.5 to the entry of the intestine having a pH of around 5.5 to 7.0 (compared to more distal sections of the small intestine having a pH of 6.0 to 7.5.

Object of the Present Invention

Therefore the object of the present invention is to provide solid dosage forms with enteric coatings where the drug release is faster at lower pH compared to state of art solid dosage forms. The object was therefore to formulate pharmaceuticals which release the contained active ingredient in accelerated fashion.

SUMMARY OF THE INVENTION

The object is solved by a solid dosage form comprising an inner coating located between a core containing a pharmaceutically active ingredient and an outer enteric coating;
wherein said inner coating comprises a partially neutralized anionic polymeric material, and at least a carboxylic acid having 2 to 16 carbon atoms the salts thereof or mixtures of said acid and its salt;
wherein said outer coating comprises an anionic polymeric material which is less or not at all neutralized than the material of the inner coating.

The present invention provides an enteric-coated solid dosage form.

As enteric-coated solid dosage form the dosage form according to the present invention is gastric resistant and shows less than 10 percent drug release in a simulated gastric fluid for at least 120 min according to USP 28. For example, this test for showing gastric resistance may be performed in a hydrochloride solution pH 1.2.

In detail, the enteric-coated solid dosage form of the present invention is acid resistant (gastric resistant) and shows less than 10 percent drug release and preferably essentially no drug release in a hydrochloride solution pH 1.2 for at least 120 min, before it, for example, is placed into a phosphate buffer of higher pH, for example of pH 5.6. The present inventors have shown that the use of an inner coating which is located between the outer enteric coating and the core of the solid dosage form helps to disintegrate and to release the drug at a certain pH earlier compared to a solid dosage form having an enteric coating without inner coating. The intended effect is that in vivo the solid dosage form according to the invention releases its active substance "earlier", namely already at the entry of the intestine. The term "earlier" here means that the solid dosage form according to the invention starts to release the active substance already at lower pH value compared to the normal pH of the intestine, namely when the solid dosage form is transferred from the stomach having low pH e.g. 1.2 to the entry of the intestine (e.g. pH 5.6) which is having a higher pH compared to the stomach, but not as high as it is the case in more distal sections of the intestine.

This effect is achieved as follows: In case the inner coating is prepared from an aqueous solution or dispersion containing the respective anionic polymer therein, this solution or dispersion is having a higher pH than the solution or dispersion from which the outer coating is obtained. It should be understood that the coating as such in solid form does not have a pH. As far as herein the pH of the coating or the film is mentioned it means the pH of the solution or dispersion from which the coating is obtained. Although, there is no pH which can be measured in the solid coating the difference in pH of the solution or dispersion from which the inner coating is made is significant.

In case of the preparation the polymer from an aqueous solution or dispersion, in a preferred embodiment the pH value of the solution or dispersion from which the inner coating is obtainable is at least 0.5 pH units, more preferred at least 1.0 pH units, further preferred at least 1.5 pH units, even further preferred at least 2.0 pH units, even further preferred at least 2.5 pH units, even further preferred at least 3.0 pH units, most preferred at least 4.0 pH units higher than the pH value of the solution or dispersion from which the outer coating is obtainable.

In case the inner coating is prepared in an organic solvent there also can be no pH measured. In this case the anionic polymer for the inner coating is obtained from an (organic) solution or dispersion wherein the degree of neutralization of the anionic groups is higher compared to the solution or dispersion from which the outer coating is made.

In a preferred embodiment the difference in the neutralization between the inner coating and the outer coating is at least 5 percentage points, preferably at least 10 percentage points and most preferred at least 20 percentage points. Further preferred, the degree of neutralization of anionic groups of the outer coating is at most 10 percent, preferably at most 6 percent, further preferred at most 4 percent, even further preferred at most 2 percent and most preferred 0.

Further preferred the anionic polymeric material comprised in the inner coating and in the outer coating, respectively, is independently from each other selected from the group consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate or shellac.

Preferably, the inner coating is made of a partially neutralized anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, wherein 1 to 80% preferably at least 2 to 70% of the contained anionic groups are neutralized by an alkaline agent;

and the outer coating is made of anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group.

It is further preferred that the salt of the carboxylic acid is an alkali metal salt, more preferably a sodium or potassium salt.

In a particularly preferred embodiment the carboxylic acid is having 2 to 16 carbon atoms and even further preferred is having 1, 2 or 3 carboxyl groups. As further examples for carboxylic acids which may be present in the inner coating the following may be mentioned: sorbic acid, benzoic acid, fumaric acid, adipic acid, citric acid, succinic acid, glutaric acid, malic acid, tartaric acid, acetic acid, glycolic acid, malonic acid, propanoic acid, glyceric acid, trans-crotonic acid, itaconic acid, mesaconic acid, trimethylacetic acid, isocitric acid, hexanoic acid, 4-methylpentanoic acid, gallic acid, terephthalic acid, phenylacetic acid, mandelic acid, alpha-phenylpropanoic acid, beta-phenylpropanoic acid, lauric acid, caprylic acid, caprinic acid, myristic acid and mixtures thereof, the salts thereof or mixtures of said acid and its salt. Most preferably the carboxylic acid is adipic acid, citric acid or sorbic acid. Examples of the salt of carboxylic acids include sodium citrate. Further, particularly preferred is adipic acid or citric acid, or their salts for example sodium citrate, or a mixture of acid and its salt for example the buffer system citric acid/Na citrate. The amount of the carboxylic acid or salt thereof, or mixtures of said acid and its salt, preferably lies within the range from 5 to 35 percent by weight, more preferred in the range of 7 to 20 percent by weight based on the dry polymer of the inner coating.

It is further preferred that each the inner and the outer coating contain 2 to 10, preferred 2 to 8, most preferably 4 to 6 mg/cm$^2$ polymer weight gain. It is further particularly preferred that the relation between the inner and the outer coating is 10:90 to 90:10, preferred 30:70 to 70:30 by weight of dry polymer.

The object of the present invention is also solved by a method for the manufacture of a gastric resistant, enteric coated solid dosage form comprising the following steps:
a) a step of coating a core containing a pharmaceutically active ingredient with a polymeric material;
b) a step of coating an anionic polymeric material on top of the coating of a) to form an outer enteric coating;
so that said solid dosage form comprises an inner coating located between the core containing a pharmaceutically active ingredient and said outer enteric coating;
wherein in case of preparing the polymeric material from aqueous solutions or dispersions the pH of the solution or dispersion from which the polymeric material of the inner coating is prepared has a higher pH compared to the solution or dispersion from which the polymeric material of the outer coating is prepared; or wherein in case of preparing the polymeric material from solutions or dispersions based on organic solvents the degree of neutralization of the solution or dispersion from which the polymeric material of the inner coating is prepared is higher compared to the solution or dispersion from which the polymeric material of the outer coating is prepared;
wherein under pH conditions in the range from pH 3 to 7 where solid dosage forms comprising said outer coating but which do not comprise said inner coating achieve a release of 10 percent of the pharmaceutically active ingredient at a certain time within 2 to 5 hours, the solid dosage forms comprising said inner and said outer coating achieve a release of 10 percent of the pharmaceutically active ingredient within 80 percent of the time or less.

Further, the object of the present invention is also solved by a gastric resistant, enteric coated solid dosage form comprising
an inner coating located between the core containing a pharmaceutically active ingredient and an outer enteric coating;
wherein the inner coating comprises a polymeric material and the outer coating comprises an anionic polymeric material;
wherein in case of preparing the polymeric material from aqueous solutions or dispersions the pH of the solution or dispersion from which the polymeric material of the inner coating is prepared has a higher pH compared to the solution or dispersion from which the polymeric material of the outer coating is prepared; or wherein in case of preparing the polymeric material from solutions or dispersions based on organic solvents the degree of neutralization of the solution or dispersion from which the polymeric material of the inner coating is prepared is higher compared to the solution or dispersion from which the polymeric material of the outer coating is prepared;
wherein under pH conditions in the range from pH 3 to 7 where solid dosage forms comprising said outer coating but which do not comprise said inner coating achieve a release of 10 percent of the pharmaceutically active ingredient at a certain time within 2 to 5 hours, the solid dosage forms comprising said inner and said outer coating achieve a release of 10 percent of the pharmaceutically active ingredient within 80 percent of the time or less.

Even further, the object of the present invention is solved by the use of a polymeric material for the manufacture of a gastric resistant, enteric-coated solid dosage form,
wherein said solid dosage form comprises an inner coating located between the core containing a pharmaceutically active ingredient and an outer enteric coating;
wherein said polymeric material is comprised in the inner coating;
wherein in case of preparing the polymeric material from aqueous solutions or dispersions the pH of the solution or dispersion from which the polymeric material of the inner coating is prepared has a higher pH compared to the solution or dispersion from which the polymeric material of the outer coating is prepared; or
wherein in case of preparing the polymeric material from solutions or dispersions based on organic solvents the degree of neutralization of the solution or dispersion from which the polymeric material of the inner coating is prepared is higher compared to the solution or dispersion from which the polymeric material of the outer coating is prepared;
wherein under pH conditions in the range from pH 3 to 7 where solid dosage forms comprising said outer coating but which do not comprise said inner coating achieve a release of 10 percent of the pharmaceutically active ingredient at a certain time within 2 to 5 hours, the solid dosage forms comprising said inner and said outer coating achieve a release of 10 percent of the pharmaceutically active ingredient within 80 percent of the time or less.

Hereinafter preferred embodiments of above mentioned solid dosage form, method for its manufacture, or use of a polymeric material for the manufacture of said solid dosage form will be described:

As mentioned above, in case the inner coating is prepared from an aqueous solution or dispersion containing the respective polymer therein, this solution or dispersion is having a higher pH than the solution or dispersion from which the outer coating is obtained. It should be understood that the coating as such in solid form does not have a pH. As far as herein the pH of the coating or the film is mentioned it means the pH of the solution or dispersion from which the coating is obtained. Although, there is no pH which can be measured in the solid coating the difference in pH of the solution or dispersion from which the inner coating is made is significant.

In case the inner coating is prepared in an organic solvent there also can be no pH measured. In this case the anionic polymer for the inner coating is obtained from an (organic) solution or dispersion wherein the degree of neutralization of the anionic groups is higher compared to the solution or dispersion from which the outer coating is made.

It is preferred that in case of anionic polymeric material the difference in the neutralization of anionic groups between the inner coating and the outer coating is at least 5 percentage points, preferably at least 10 percentage points and most preferred at least 20 percentage points.

It is further preferred that the degree of neutralization of anionic groups of the outer coating is at most 10 percent, preferably at most 6 percent, further preferred at most 4 percent, even further preferred at most 2 percent and most preferred 0.

Further preferred in case of aqueous solutions or dispersions the pH value of the solution or dispersion from which the inner coating is prepared is at least 0.5 pH units, more preferred at least 1.0 pH units, further preferred at least 1.5 pH units, even further preferred at least 2.0 pH units, even further preferred at least 2.5 pH units, even further preferred at least 3.0 pH units, most preferred at least 4.0 pH units higher than the pH value of the solution or dispersion from which the outer coating is prepared.

Preferably, in case of aqueous solutions or dispersions the difference of the pH value between the solution or dispersion from which the inner coating is prepared and the solution or dispersion from which the outer coating is prepared is in the range of 2 to 4 pH units.

It is particularly preferred that the inner coating is further comprising a carboxylic acid having 2 to 16 carbon atoms or inorganic acids, the salts thereof or mixtures of said acid and its salt. Preferably, the salt is an alkali metal salt.

It is further preferred that the carboxylic acid is selected from the group consisting of sorbic acid, benzoic acid, fumaric acid, adipic acid, citric acid, succinic acid, glutaric acid, malic acid, tartaric acid, acetic acid, glycolic acid, malonic acid, propanoic acid, glyceric acid, trans-crotonic acid, itaconic acid, mesaconic acid, trimethylacetic acid, isocitric acid, hexanoic acid, 4-methylpentanoic acid, gallic acid, terephthalic acid, phenylacetic acid, mandelic acid, alpha-phenylpropanoic acid, beta-phenylpropanoic acid, lauric acid, caprylic acid, caprinic acid, myristic acid and mixtures thereof, the salts thereof or mixtures of said acid and its salt. It is particularly preferred that the carboxylic acid is adipic acid or citric acid. Examples of the salt of carboxylic acids include sodium citrate. The amount of the carboxylic acid or salt thereof, or mixtures of said acid and its salt, preferably lies within the range from 5 to 35 percent by weight, more preferred in the range of 7 to 20 percent by weight based on the dry polymer of the inner coating. The inventors found that the presence of organic or inorganic acids, particularly carboxylic acid having 2 to 16 carbon atoms and having 1, 2 or 3 carboxyl groups, more particularly adipic acid or citric acid, but also their salts (e.g. Na citrate) in the inner coating further accelerates the drug release rate.

Further preferred, the polymeric material of the inner coating is an anionic polymeric material, or a water soluble polymer selected from the group consisting of hydroxypropyl cellulose, hydroxypropyl methylcellulose, poly(ethylenoxide)-graft-polyvinylalcohol, polyvinylpyrollidone (PVP), polyethylene glycol (PEG) and/or polyvinyl alcohol.

In a preferred embodiment of the invention the anionic polymeric material comprised in the inner coating is selected from the group consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate or shellac.

Preferably, the anionic polymeric material comprised in the inner coating is a partially neutralized anionic (meth) acrylate copolymer consisting of free-radical polymerized units of 25 to 95% by weight $C_1$- to $C_4$-alkyl esters of acrylic or of methacrylic acid and 5 to 75% by weight (meth) acrylate monomers having an anionic group, wherein 1 to 80% preferably at least 2 to 70% of the contained anionic groups are neutralized by an alkaline agent.

Further preferred, the anionic polymeric material comprised in the outer coating is selected from the group consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate or shellac.

In a further preferred embodiment the anionic polymeric material comprised in the outer coating is an anionic (meth) acrylate copolymer consisting of free-radical polymerized units of 25 to 95% by weight $C_1$- to $C_4$-alkyl esters of acrylic or of methacrylic acid and 5 to 75% by weight (meth) acrylate monomers having an anionic group, wherein the outer coating is less neutralized than the inner coating or not at all neutralized.

Furthermore preferred the outer and the inner coating comprises an anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, wherein the outer coating is less neutralized than the inner coating or not at all neutralized, wherein the inner coating is further comprising carboxylic acids or inorganic acids, the salts thereof or mixtures thereof.

It is particularly preferred that each the inner and the outer coating contain 2 to 10, preferred 2 to 8, most preferably 4 to 6 mg/cm$^2$ polymer weight gain. Preferably the relation between the inner and the outer coating is 10:90 to 90:10, preferred 30:70 to 70:30 by weight of dry polymer.

Further Embodiments

The object of the present invention is also solved by a gastric resistant, enteric-coated solid dosage form comprising an inner coating located between a core containing a pharmaceutically active ingredient and an outer enteric coating;
wherein said inner coating comprises a polymeric material selected from the group consisting of an anionic polymeric material or a water soluble neutral polymer;
wherein said inner coating further comprises at least a water soluble inorganic salt, with the proviso that carbonates and bicarbonates are excluded;
wherein said outer coating comprises an anionic polymeric material which is less or not at all neutralized than the material of the inner coating.

In case of preparing the polymeric material from aqueous solutions or dispersions the pH of the solution or dispersion from which the polymeric material of the inner coating is prepared has a higher pH compared to the solution or dispersion from which the polymeric material of the outer coating is prepared. In case of preparing the polymeric material from solutions or dispersions based on organic solvents the degree of neutralization of the solution or dispersion from which the polymeric material of the inner coating is prepared is higher compared to the solution or dispersion from which the polymeric material of the outer coating is prepared.

As mentioned above, in case the inner coating is prepared from an aqueous solution or dispersion containing the respective polymer therein, this solution or dispersion is having a higher pH than the solution or dispersion from which the outer coating is obtained. It should be understood that the coating as such in solid form does not have a pH. As far as herein the pH of the coating or the film is mentioned it means the pH of the solution or dispersion from which the coating is obtained. Although, there is no pH which can be measured in the solid coating the difference in pH of the solution or dispersion from which the inner coating is made is significant.

In case the inner coating is prepared in an organic solvent there also can be no pH measured. In this case the anionic polymer for the inner coating is obtained from an (organic) solution or dispersion wherein the degree of neutralization of the anionic groups is higher compared to the solution or dispersion from which the outer coating is made.

It is preferred that in case of anionic polymeric material the difference in the neutralization of anionic groups between the inner coating and the outer coating is at least 5 percentage points, preferably at least 10 percentage points and most preferred at least 20 percentage points.

It is further preferred that the degree of neutralization of anionic groups of the outer coating is at most 10 percent, preferably at most 6 percent, further preferred at most 4 percent, even further preferred at most 2 percent and most preferred 0.

Further preferred in case of aqueous solutions or dispersions the pH value of the solution or dispersion from which the inner coating is prepared is at least 0.5 pH units, more preferred at least 1.0 pH units, further preferred at least 1.5 pH units, even further preferred at least 2.0 pH units, even further preferred at least 2.5 pH units, even further preferred at least 3.0 pH units, most preferred at least 4.0 pH units higher than the pH value of the solution or dispersion from which the outer coating is prepared.

Preferably, in case of aqueous solutions or dispersions the difference of the pH value between the solution or dispersion from which the inner coating is prepared and the solution or dispersion from which the outer coating is prepared is in the range of 2 to 4 pH units.

Preferably, the water soluble neutral polymer is selected from the group consisting of hydroxypropyl cellulose, hydroxypropyl methylcellulose, poly(ethylenoxide)-graft-polyvinylalcohol, polyvinylpyrollidone (PVP), polyethylene glycol (PEG) and/or polyvinyl alcohol. Further preferred, the anionic polymeric material is selected from the group consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate or shellac.

It is particularly preferred that the inorganic salt is selected from alkali metal salt, earth alkali metal salt, ammonium salt, soluble metal salts. As metals for the soluble metal salts manganese, iron, copper, zinc and molybdenum can be mentioned. Further preferred, the inorganic salt is selected from chloride, fluoride, bromide, iodide, phosphate, nitrate, nitrite, sulphate, borate, for example NaCl, KCl, NH4Cl, NaI, KI, NaF, KF.

In a further preferred embodiment the anionic polymeric material comprised in the inner coating is a partially neutralized anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, wherein 1 to 80% preferably at least 2 to 70% of the contained anionic groups are neutralized by an alkaline agent.

Furthermore preferred, the anionic polymeric material comprised in the outer coating is an anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, wherein the outer coating is less neutralized than the inner coating or not at all neutralized.

Preferably, the outer and the inner coating comprises an anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, wherein the outer coating is less neutralized than the inner coating or not at all neutralized.

Further preferred each the inner and the outer coating contain 2 to 10, preferred 2 to 8, most preferably 4 to 6 mg/cm$^2$ polymer weight gain. Preferably, the relation between the inner and the outer coating is 10:90 to 90:10, preferred 30:70 to 70:30 by weight of dry polymer.

MODE OF OPERATION OF THE INVENTION

Suitable anionic polymers for the inner and the outer coating for example are anionic (meth)acrylate copolymers. Anionic (meth)acrylate copolymers, e.g. of the EUDRAGIT® L, EUDRAGIT® L 100-55, EUDRAGIT® S or EUDRAGIT®FS type, are known as coatings which are soluble in intestinal juice for pharmaceutical forms. Depending on the monomer composition, but especially depending on the content of anionic groups, the anionic (meth)acrylate copolymers are characterized by specific pH values for dissolution in intestinal juice or in simulated intestinal fluid. Depending on the polymer type, the specific pH values for dissolution, or the pH values for the specific start of dissolution, are in the range of for example pH 5.5 to 7.5. At and above the specific pH for dissolution of the respective anionic (meth)acrylate copolymer, pharmaceutical forms coated therewith release the contained active ingredient. The specific pH values for dissolution thus characterize the start of the release of active ingredient.

It is known to employ anionic (meth)acrylate copolymers in partially neutralized form as single layer in order to improve the stability of acid-labile active agents. An improved solubility of the polymer in water and a stabilization of the polymer dispersions is achieved thereby. Bases which can be used for the partial neutralization are normally substances such as NaOH, KOH, ammonium hydroxide or organic bases such as, for example, triethanolamine.

Comparison of films of anionic (meth)acrylate copolymers which have been partially neutralized for example by means of NaOH, and which have not been partially neutralized, reveals that the partially neutralized films dissolve more rapidly in a buffer system at their specific pH for dissolution than the non-neutralized films. However, a neutralization necessary to raise pH abolished the necessary resistance to gastric juice of the pharmaceutical composition.

Anionic (Meth)Acrylate Copolymer

In a preferred embodiment anionic (meth)acrylate copolymers are used for both the outer and the inner coating. If anionic (meth)acrylate copolymers are used for the inner coating they are partially neutralized. The anionic (meth)acrylate copolymer comprises 25 to 95, preferably 40 to 95, in particular 60 to 40, % by weight free-radical polymerized $C_1$- to $C_4$-alkyl esters of acrylic or of methacrylic acid and 75 to 5, preferably 60 to 5, in particular 40 to 60, % by weight (meth)acrylate monomers having an anionic group.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, to be present. It is preferred that no further monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid, with preference for methacrylic acid.

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L 100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl meth-acrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate 0 to 10% by weight further monomers capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C.

Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and more than 10 to 30, preferably 15 to 25, particularly preferably 18 to 22% by weight butyl methacrylate, where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of the Anionic (Meth)Acrylate Copolymers

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80 000 to 1 000 000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must before processing be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Partial Neutralization

Bases suitable for the purposes of the invention are those expressly mentioned in EP 0 088 951 A2 or WO 2004/096185 or derivable therefrom. The following are excluded in particular: sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane.

Further suitable cationic, organic bases are basic amino acids histidine, arginine and/or lysine.

Adjustment of the Degree of Partial Neutralization by Mixtures

Mixtures may also result in technical advantages in the adjustment of the degree of partial neutralization. In a preferred embodiment of the invention for the inner coating it is made use of mixtures of anionic (meth)acrylate copolymers differing in the degree of partial neutralization, consisting of free-radical polymerized units of 25 to 95% by weight $C_1$- to $C_4$-alkyl esters of acrylic or of methacrylic acid and 5 to 75% by weight (meth)acrylate monomers having an anionic group, wherein 1 to 80% of the contained anionic groups, as calculated average for the mixture, are neutralized by a base. It is possible for example to mix an anionic (meth)acrylate copolymer which is not partially neutralized and consists of free-radical polymerized units of 25 to 95% by weight $C_1$- to $C_4$-alkyl esters of acrylic or of methacrylic acid and 5 to 75% by weight (meth)acrylate monomers having an anionic group with a partially neutralized (meth)acrylate copolymer of the same monomer composition within the stated quantitative ranges so that 1 to 80% of the contained anionic groups, as calculated average for the mixture, are neutralized. The mixture can be prepared for example by stirring a powder which has been obtained from a dispersion of a partially neutralized, anionic (meth)acrylate copolymer, e.g. by spray drying or freeze drying, into a dispersion of an anionic (meth)acrylate copolymer which has not been partially neutralized.

Mixtures

The (meth)acrylate copolymer which has been partially neutralized according to the invention is further suitable for mixing with other pharmaceutically utilized copolymers in order to modify the properties thereof. This increases the scope for configuration by the skilled person when adjusting specifically modified release profiles. The invention accordingly relates to a partially neutralized (meth)acrylate copolymer, characterized in that it is present in a mixture with copolymers of methyl methacrylate and/or ethyl acrylate and where appropriate less than 5% by weight methacrylic acid, copolymers of methyl methacrylate, butyl methacrylate and dimethylethyl methacrylate, copolymers of methyl methacrylate, ethyl acrylate and trimethylammoniumethyl methacrylate, copolymers of methyl methacrylate and ethyl acrylate, polyvinylpyrrolidones (PVP), polyvinyl alcohols, polyvinyl alcohol-polyethylene glycol graft copolymers (Kollicoat®), starch and its derivatives, polyvinyl acetate phthalate (PVAP, Coateric®), polyvinyl acetate (PVAc, Kollicoat), vinyl acetate-vinylpyrrolidone copolymer (Kollidon® VA64), vinyl acetate: crotonic acid 9:1 copolymer (VAC:CRA, Kollicoat® VAC), polyethylene glycols having a molecular weight above 1000 (g/mol), chitosan, a crosslinked and/or noncrosslinked polyacrylic acid, an Na alginate, and/or a pectin.

Dispersions

The non-neutralized or the partially neutralized (meth)acrylate copolymer may be for example in the form of an aqueous dispersion with a solids content of from 10 to 50 percent.

The non-neutralized or the partially neutralized (meth) acrylate copolymer may be in the form of a redispersible powder which has been obtained from a dispersion for example by spray drying.

Dispersions/partial Neutralization

The emulsion polymer is preferably produced and used in the form of a 10 to 50 percent by weight, in particular 20 to 40%, aqueous dispersion. A solids content of 30% by weight is preferred as commercial form. Partial neutralization of the methacrylic acid units can be dispensed with for processing; it is, however, possible, for example to an extent of up to 5 or 10 mol %, if a stabilization or thickening of the coating agent dispersion is desirable. The weight-average size (radius) of the latex particles is normally 40 to 100 nm, preferably 50 to 70 nm, thus ensuring a viscosity below 1000 mPa·s which is favourable for processing techniques. The particle size can be determined by laser diffraction, e.g. using the Mastersizer 2000 (from Malvern).

With higher degrees of neutralization, e.g. 10 to 50 mol %, or complete neutralization it is possible to convert the copolymer into a dissolved state.

In order to prepare a solution of the anionic copolymer it is normally necessary for the acidic groups to be partially or completely neutralized. The anionic copolymer may for example be stirred gradually in a final concentration of from 1 to 40% by weight into water and, during this, be partially or completely neutralized by adding a basic substance according to the invention such as, for example NaOH. It is also possible to employ a powder of the copolymer, to which a base has already been added during its preparation for the purpose of (partial) neutralization, so that the powder is already a (partially) neutralized polymer. The pH of the solution is normally above 4, e.g. in the range from 4 to about 8. It is also possible in this connection for batches of completely or partially neutralized dispersions to be mixed for example with non-neutralized dispersions and further processed in the manner described, i.e. use the mixture for coatings or initially freeze dry or spray dry to give a powder.

The dispersion may also for example be spray dried or freeze dried in a manner known per se and be provided in the form of a redispersible powder (see, for example, EP-A 0 262 326). Alternative processes are freeze drying or coagulation and squeezing out the water in an extruder with subsequent granulation (see, for example, EP-A 0 683 028).

Copolymer dispersions of spray-dried or freeze-dried and redispersed powders may exhibit an increased shear stability. This is advantageous in particular for spray application. This advantage is strongly evident in particular when the copolymer present in the dispersion is partially neutralized to the extent of 2 to 10, preferably 5 to 7, mol % (based on the acidic groups present in the copolymer). An anionic emulsifier is preferably present in an amount of 0.1 to 2% by weight. Sodium lauryl sulphate is particularly preferred as emulsifier.

Use of the Partially Neutralized (Meth)Acrylate Copolymers

The partially neutralized anionic (meth)acrylate copolymer can be used as coating agent for the inner coating for a pharmaceutical form which, in the USP 28 release test after 2 hours at pH 1.2 and a subsequent change in the buffer to the pH of the start of active ingredient release, releases 90%, preferably 95 or 100% of the contained active ingredient in not more than 80%, preferably not more than 75%, further preferred not more than 50% in particular not more than 25% of the time which elapses therefor with a comparable pharmaceutical having an outer enteric coating but without the inner coating of or partial neutralized (meth)acrylate copolymer.

If the pharmaceutical form not according to the invention releases in the USP 28 release test after 2 hours at pH 1.2 and a subsequent change in the buffer to the pH of the start of active ingredient release, e.g. pH 5.6, 10% or less of the active ingredient in, for example, further 250 min, a comparable pharmaceutical form according to the invention requires not more than for example 55 min (22% of the time), not more than for example 35 min (14% of the time) or not more than for example 15 min (6% of the time) therefor.

If the pharmaceutical form not according to the invention releases in the USP 28 release test after 2 hours at pH 1.2 and a subsequent change in the buffer to the pH of the start of active ingredient release, e.g. pH 5.6, 10% or less of the active ingredient in, for example, further 250 min, a comparable pharmaceutical form according to the invention requires not more than for example 80 min (32% of the time), not more than for example 50 min (20% of the time) or not more than for example 30 min (12% of the time) to release at least 30% of the active ingredient.

The USP 28 release test, in particular by USP 28 <711> paddle method (=Apparatus 2), is sufficiently well known to the skilled person.

The typical test procedure is as follows:
1. The vessels of the release apparatus are each charged with 900 ml of 0.1 M-HCl (pH 1.2) and the temperature of the waterbath is adjusted to 37±0.5° C.
2. The paddle stirrer is switched on with a rotation rate of 50 rpm.
3. 1 tablet or a certain amount of pellets containing a comparable amount of active ingredient as 1 tablet is put into each vessel of the apparatus. Care is taken that there are no air bubbles on the pellet or tablet surface.
4. After 120 min, tablets or pellets are removed from the acid, and put into 900 ml phosphate buffer solution with pH values of pH 5.5; 5.6; 5.8; 6.0 or 7.0.
5. Determination of the percentage of active ingredient release as a function of time, depending on the active ingredient, e.g. by photometry at 271 nm in the case of theophylline, or 247 nm in the case of prednisolone, in the circulating method.

Pharmaceutical Form

In a preferred embodiment of the invention a pharmaceutical form is comprising a core having an active pharmaceutical ingredient and comprising a inner polymer coating of a partially neutralized (meth)acrylate copolymer and an outer coating of (meth)acrylate copolymer which is not at all neutralized or less neutralized.

The pharmaceutical form may preferably comprise a polymer coating with NaOH as neutralizing agent in combination with 0 to 70% by weight of a plasticizer. The pharmaceutical form may further preferably comprise a polymer coating with an organic acid such as citric acid (preferably 10 to 30% by weight) and NaOH as neutralizing agent in combination with 5 to 25% by weight of a plasticizer or a mixture of Na citrate and citric acid (preferably 10 to 30% by weight) in combination with 5 to 25% by weight of a plasticizer.

The corresponding pharmaceutical form may be for example in the form of a multiparticulate pharmaceutical form, pellet-containing tablets, minitablets, capsules, sachets, effervescent tablets or reconstitutable powders.

Process for Producing a Pharmaceutical Form

The invention further relates to a process for producing the pharmaceutical form according to the invention in a manner known per se by pharmaceutically customary processes such as direct compression, compression of dry, wet or sintered granules, extrusion and subsequent rounding off, wet or dry granulation or direct pelleting or by binding powders (powder layering) onto active ingredient-free beads or neutral cores (nonpareils) or active ingredient-containing particles and by applying the polymer coating in a spray process or by fluidized bed granulation.

Production of Multiparticulate Pharmaceutical Forms

The invention is suitable in particular for producing multiparticulate pharmaceutical forms, because the copolymer according to the invention withstands the high pressures in the compression of the pellets with the filler.

The production of multiparticulate pharmaceutical forms by compression of a pharmaceutically usual binder with active ingredient-containing particles is described in detail for example Beckert et al. (1996), "Compression of enteric-coated pellets to disintegrating tablets", *International Journal of Pharmaceutics* 143, pp. 13-23, and in WO 96/01624.

Active ingredient-containing pellets can be produced by applying active ingredient by means of a layering process. For this purpose, active ingredient is homogenized together with further excipients (release agent, where appropriate plasticizer) and dissolved or suspended in a binder. The liquid can be applied by means of a fluidized bed process to placebo pellets or other suitable carrier materials, with evaporation of the solvent or suspending agent (literature: *International Journal of Pharmaceutics* 143, pp. 13-23). The production process may be followed by a drying step. The active ingredient can be applied in a plurality of layers.

Some active ingredients, e.g. acetylsalicylic acid, are commercially available in the form of active ingredient crystals and can be employed in this form instead of active ingredient-containing pellets.

Film coatings on active ingredient-containing pellets are normally applied in fluidized bed apparatuses. Formulation examples are mentioned in this application. Film formers are normally mixed with plasticizers and release agents by a suitable process. It is possible in this case for the film formers to be in the form of a solution or suspension. The excipients for the film formation may likewise be dissolved or suspended. Organic or aqueous solvents or dispersants can be used. It is additionally possible to use stabilizers to stabilize the dispersion (for example: Tween 80 or other suitable emulsifiers or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

According to the invention there is located between the active ingredient-containing core and the intestine-soluble copolymer layer (outer coating) an inner coating, which may consist of inert film formers (e.g. HPMC, HPC or (meth) acrylic acid copolymers) or, for example, talc or other suitable pharmaceutical substances. It is likewise possible to use combinations of film formers and talc or similar substances.

Mixtures for producing tablets from coated particles are prepared by mixing the pellets with suitable binders for tableting, if necessary adding disintegration-promoting substances and if necessary adding lubricants. The mixing can take place in suitable machines. Unsuitable mixers are those leading to damage to the coated particles, e.g. ploughshare mixers. A specific sequence of addition of the excipients to the coated particles may be necessary to achieve suitable short disintegration times. It is possible by premixing with the coated particles with the lubricant or mould release agent magnesium stearate for its surface to be rendered hydrophobic and thus for adhesion to be avoided.

Mixtures suitable for tableting normally comprise 3 to 15% by weight of a disintegration aid, e.g. Kollidon CL and, for example, 0.1 to 1% by weight of a lubricant and mould release agent such as magnesium stearate. The binder content is determined by the required proportion of coated particles.

Examples of typical binders are Cellactose®, microcrystalline cellulose, calcium phosphates, Ludipress®, lactose or other suitable sugars, calcium sulphates or starch derivatives. Substances of low apparent density are preferred.

Typical disintegration aids (disintegrants) are crosslinked starch or cellulose derivatives, and crosslinked polyvinylpyrrolidone. Cellulose derivatives are likewise suitable. The use of disintegration aids can be dispensed with through selection of a suitable binder.

Typical lubricants and mould release agents are magnesium stearates or other suitable salts of fatty acids or substances mentioned in the literature for this purpose (e.g. lauric acid, calcium stearate, talc, etc.). The use of a lubricant and mould release agent in the mixture can be dispensed with on use of suitable machines (e.g. tablet press with external lubrication), or suitable formulations.

A flow-improving aid can be added where appropriate to the mixture (e.g. colloidal silica derivatives, talc etc.).

The tableting can take place on conventional tablet presses, eccentric or rotary tablet presses, with compressive forces in the range from 5 to 40 kN, preferably 10-20 kN. The tablet presses may be equipped with systems for external lubrication. Special systems for die filling which avoid die filling by means of impeller paddles are employed where appropriate.

Further Processes for Producing the Pharmaceutical Form According to the Invention Application process takes place by spray application from organic solution or preferably aqueous dispersions by melting or by direct powder application. The crucial factor for the implementation in this case is that uniform, pore-free coatings result.

For prior art application processes see, for example, Bauer, Lehmann, Osterwald, Rothgang, "Überzogene Arzneiformen" Wissenschaftliche Verlagsgesellschaft mbH, Stuttgart, Chapter 7, pp. 165-196

Relevant properties, required tests and specifications for the application are listed in pharmacopoeias.

Details are to be found in the customary textbooks, for example:

Voigt, R. (1984): Lehrbuch der pharmazeutischen Technologie; Verlag Chemie Weinheim Beerfield Beach/Florida Basle.

Sucker, H., Fuchs, P., Speiser, P.: Pharmazeutische Technologie, Georg Thieme Verlag Stuttgart (1991), especially Chapters 15 and 16, pp. 626-642.

Gennaro, A. R. (editor), Remington's Pharmaceutical Sciences, Mack Publishing Co., Easton Pa. (1985), Chapter 88, pp. 1567-1573.

List, P. H. (1982): Arzneiformenlehre, Wissenschaftliche Verlagsgesellschaft mbH, Stuttgart.

The present invention will be further explained in more detail by the following examples, which are understood not to limit the scope of the invention in any way.

EXAMPLES

1. General Findings

In order to find a solution to the object of the present invention the inventors found that for example a dispersion of Eudragit® L 30D-55 containing 10 percent by weight adipic acid, which was neutralized to pH 5.6 could change to a clear solution and the so cast film dissolved very fast in pH 5.8 phosphate buffer. The respective film swelled and turned to clear within 5 min. However, neutralized adipic acid could leach out from the film in 0.1M HCl, which makes the film performance in subsequent phosphate buffer no difference as control film.

Further exploration resulted in the present invention. According to the present invention the application of a normal Eudragit® L 30D-55 coat on top of the neutralized adipic acid-containing coat of solid dosage forms, the outer Eudragit® coat protects the inner coat containing adipic acid in 0.1M HCl. During the subsequent treatment of the respective pellets or tablets in phosphate buffer having for example a pH of 5.6, the buffer solution will diffuse through the outer coat and contact the inner coat. As result the adipic acid-containing inner coat could dissolve very fast and assumingly could diffuse into the outer coat, therefore helping to break down the outer coat as well and to release the drug.

2. Materials

Prednisolone was purchased from Aventis Pharma., Antony, France. Theophylline pellets (1.00-1.25 mm) were purchased from Klinge Pharm. Lactose (Pharmatose, 110 μm) was purchased from Ellis & Everard, Essex, UK. Sodium carboxymethylcellulose (Ac-di-sol) was donated by FMC International, Cork, Eire. Polyvinylpyrrolidone (PVP) was purchased from VWR International Ltd, Poole, UK. Eudragit® L 30D-55 (Röhm GmbH & Co. KG, Darmstadt, Germany). HPMC E5 (hydroxylpropyl methylcellulose) was donated by Colorcon Inc., Dartford, UK. HP-55 (hydroxypropyl methylcellulose phthalate) was purchased from Shin-Etsu Chemical Co., Ltd, Tokyo, Japan. Triethyl citrate (TEC) was purchased from Lancaster Synthesis, Lancashire, UK. All other reagents were purchased from Sigma, St. Louis, Mo., USA.

3. Preparation of Prednisolone Tablets and Pellets

As solid dosage form tablets containing the active substance Prednisolone were used in the tests. The round tablets (representing the core of the solid dosage form) with a diameter of 8 mm were prepared by wet granulation. Each tablet contains 5% by weight prednisolone (10 mg), 88.5% by weight lactose, 5 by weight PVP, 0.5 percent Ac-di-sol and 1% by weight magnesium stearate. The obtained tablets are further coated by the respective layers.

Prednisolone pellets (0.71-1.0 mm) were prepared by extrusion and spheronisation. Each pellet contains 35% by weight prednisolone, 40% by weight lactose and 25% by weight Avicel PH101.

4. Coating for Prednisolone Tablets and Pellets

Prednisolone tablets and pellets were coated in fluid bed (Strea-1, Aeromatic).

4.1 Coating Formulations

Eudragit® L 30D-55 with Organic Acid Inner Coating:

Adipic and citric acid, respectively, (5 to 30%, based on polymer weight), 5% triethylcitrate (TEC) based on polymer weight were dissolved in water, and added into Eudragit® L30D-55 dispersions. The above dispersions were then neutralised to pH 5.6, 5.8 or 6.0 using 1 M NaOH and the dispersions turned to clear solutions. 50% talc based on the polymer weight was homogenised in water and added to above solution. The total solid content of the coating dispersion was 10%. 5 mg/cm$^2$ of polymer was applied.

Eudragit® L100 with Organic Acid Inner Coating

10% citric acid and 50% TEC (both based on polymer weight) were dissolved in water. Eudragit® L100 was dispersed in above solution, and neutralized to clear solution with pH 6.2 or 6.8.50% Talc based on polymer weight was homogenized in water and added to above solution. The total solid content of the coating dispersion was 10%. 5 mg/cm$^2$ of polymer was applied.

HPMC as Coating:

10% by weight HPMC E5 solutions with or without 10% by weight Na citrate, 10% citric acid, 10% NaCl were used. 1, 3, 5 mg/cm$^2$ of polymer were applied.

Eudragit® L 30D-55 Control and Outer Coating:

10% TEC (based on polymer weight) was dissolved in water, and added into Eudragit® L 30D-55 dispersion. 50% talc based on polymer weight was homogenized in water and added into above dispersion. The total solid content of the coating dispersion was 20%. 5 mg/cm$^2$ of polymer was applied.

HP-55 Coating (Hydroxypropyl Methylcellulose Phthalate)

6% HP-55 solution was prepared by dissolving in ethonal/water (80:20). 5 mg/cm$^2$ of polymer was applied.

4.2 Coating Conditions

Table 2 summarizes the coating conditions for prednisolone tablets and table 3 summarizes the coating conditions for prednisolone pellets.

Table 2 Shows the Coating Conditions for Prednisolone Tablets.

| Formulations | Inlet temperature (° C.) | Outlet temperature (° C.) | Capacity of fan | Atomizing pressure (bar) | Flow rate (ml/min) |
|---|---|---|---|---|---|
| L 30D-55, organic acid inner coat | 40 | 30 | 15 | 0.2 | 0.5-1.5 |
| L100/S100/FS inner coat | 40 | 30 | 15 | 0.2 | 1.5 |
| HPMC E5 subcoating | 40 | 30 | 15 | 0.2 | 1.5 |
| L 30D-55 control and outer coating | 40 | 30 | 15 | 0.2 | 2.0 |
| HP-55 coating | 45 | 35 | 15 | 0.2 | 2.0 |

Table 3 shows the coating conditions for prednisolone pellets.

| Formulations | Inlet temperature (° C.) | Outlet temperature (° C.) | Capacity of fan | Atomizing pressure (bar) | Flow rate (ml/min) |
|---|---|---|---|---|---|
| L 30D-55, organic acid inner coating | 40 | 30 | 15 | 0.6 | 1.5 |
| HPMC subcoating | 45 | 35 | 15 | 2.0 | 1.5 |
| L 30D-55 control and outer coating | 40 | 30 | 15 | 0.6 | 2 |

5. Coating for Theophylline Pellets

Theophylline pellets were coated in fluid bed (Huettlin Mycrolab).

5.1 Coating Formulations

Eudragit L 30D-55 with 10% Citric Acid Inner Coating:

10% citric acid (based on polymer weight), 5% triethylcitrate (TEC) (based on polymer weight) were dissolved in water, and added into EUDRAGIT® L30 D-55 dispersions. The above dispersions were then neutralised to pH 5.6 using 1 M NaOH and the dispersions turned to clear solutions. 50% Talc based on polymer weight was homogenised in water and added to above solution. The total solid content of the coating dispersion was 10%. 5 mg/cm$^2$ of polymer was applied.

Eudragit L 30D-55 Control and Outer Coating:

10% TEC (based on polymer weight) was dissolved in water, and added into Eudragit L 30 D-55 dispersion. 50% talc based on polymer weight was homogenized in water and added into above dispersion. The total solid content of the coating dispersion was 20%. 5 mg/cm$^2$ of polymer was applied.

4.2 Coating Conditions

Eudragit L 30D-55 with 10% Citric Acid Inner Coating:

Inlet air temperature: 38.0-40.0° C.; product temperature: 28-30° C.; Exhaust air temperature: 27-29° C.; exhaust air humidity: 25-38%; micro climate: 0.6 bar; airflow: 20.0 m$^3$/h; atomizing air pressure: 1.6-2.3 bar; spray rate: 2.2 g/min.

Eudragit L 30D-55 Control and Outer Coating:

Inlet air temperature: 40.0-45.0° C.; product temperature: 28-30° C.; Exhaust air temperature: 22-27° C.; exhaust air humidity: 40-45%; micro climate: 0.4 bar; airflow: 16.0-18.0 m$^3$/h; atomizing air pressure: 0.6-0.8 bar; spray rate: 2.2 g/min.

6. Dissolution Tests for Eudragit® Coated Tablets and Pellets, Comprising as Active Ingredient Prednisolone or Theophylline, Respectively Dissolution test for coated tablets and pellets comprising as active ingredient prednisolone or theophylline, respectively, were carried out using BP Method II paddle apparatus (Model PTWS, Pharmatest, Hainburg, Germany). The volume of the dissolution media was 900 ml maintained at 37±0.5° C. and a paddle speed of 50 rpm was employed. The amount of prednisolone or theophylline released from the coated tablets or pellets was determined by UV spectrophotometer at 247 nm for prednisolone or at 271 nm for theophylline, respectively. Tablets or pellets were placed for 120 min into 0.1N HCl, and subsequently into different pH of phosphate buffer.

Example 1

Effects of Different Acid Concentrations in the Inner Coat on Drug Release from Double Coating System The present example shows the effects of different adipic acid concentration in the inner coat (pH 5.6) on the drug release. For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 5 mg/cm$^2$, 10, 15 and 20% by weight adipic acid, respectively, pH 5.6. The tablets were subjected to a solution of 0.1 N HCl for 2 h and subsequently to a phosphate buffer pH 5.6.

The drug release rate was strongly increased when using adipic acid concentration in the inner coat of 10%, 15% and 20% by weight compared to the control solid dosage form having the same outer coating but which does not comprise an inner coating (data not shown). Further, it was observed that the coating process using Eudragit® L 30D-55 neutralised to pH 5.6 further comprising adipic acid as the inner coat was easy, and the higher the adipic acid concentration, the easier was the coating process.

Further experiments were carried out with the following prednisolone-containing tablets: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 10, 15, 20 and 30% by weight citric acid, respectively, pH 5.6. The tablets were subjected to a solution of 0.1 N HCl for 2 h and subsequently to a phosphate buffer pH 5.6.

Table 4 summarizes a comparison of different citric acid concentrations in the inner coat. The drug releases from 10% by weight citric acid double coated tablets were faster than from 10% adipic acid double coated tablets (s. table 5). In pH 5.6 buffer, the drug release differences of 10, 15, 20, 30% citric acid formulations were very small.

In buffer having pH 5.5 15% the citric acid formulation showed faster drug release than 10% citric acid (data not shown).

Table 4 shows the dissolution profiles of citric acid-containing Eudragit® L 30D-55 double coated prednisolone tablets in 0.1N HCl for 2 h and subsequent pH 5.6 phosphate buffer (all the formulations have the same outer coat: Eudragit® L30D-55, 5 mg/cm$^2$).

| time [min] | Control: Eudragit ®L30D-55 enteric coating; no inner coating | outer coating: Eudragit ®L30D-55 inner coating: Eudragit ®L30D-55 10% by weight citric acid, pH 5.6 | outer coating: Eudragit ®L30D-55 inner coating: Eudragit ®L30D-55 15% by weight citric acid, pH 5.6 | outer coating: Eudragit ®L30D-55 inner coating: Eudragit ®L30D-55 20% by weight citric acid, pH 5.6 | outer coating: Eudragit ®L30D-55 inner coating: Eudragit ®L30D-55; 30% by weight citric acid, pH 5.6 |
|---|---|---|---|---|---|
| 120 | 0.0 | 0.0 | 0.0 | 0.0 | 0.0 |
| 150 | 0.0 | 0.5 | 1.1 | 1.1 | 2.4 |
| 155 | 0.0 | 1.0 | 2.0 | 4.9 | 7.8 |
| 160 | 0.0 | 2.8 | 5.5 | 6.9 | 17.3 |
| 165 | 0.0 | 7.1 | 14.1 | 9.0 | 21.1 |
| 170 | 0.0 | 12.7 | 24.7 | 13.2 | 26.3 |
| 180 | 0.0 | 32.9 | 48.8 | 63.1 | 34.8 |
| 195 | 0.0 | 62.8 | 72.0 | 87.0 | 41.0 |
| 240 | 1.1 | 103.8 | 94.0 | 94.6 | 89.2 |
| 375 | 10.0 | 106.8 | 97.1 | 99.3 | 98.1 |

Example 2

Effects of Different Amounts of Outer Coat

In this experiment the effects of application of different amounts of outer coating on the dissolution was investigated. For this experiment the following prednisolone-containing tablets were used: i) control tablets containing Eudragit® L 30D-55, 3, 4 and 5 mg/cm², respectively; ii) double-coated tablets comprising outer coating Eudragit® L 30D-55, 3, 4 and 5 mg/cm², respectively; inner coating of Eudragit® L 30D-55, 20% by weight citric acid, pH 5.6. The tablets were subjected to a solution of 0.1 N HCl for 2 h and subsequently to a phosphate buffer pH 5.6.

It was shown that the dissolution rate of an outer coating of 5 mg/cm² (30% release was achieved within 175 min, 50% release was achieved within 180 min) was higher than that of 4 mg/cm² (30% release within 175 min, 50% release within 220 min), which again was higher than that of 3 mg/cm² outer coat (30% release within 340 min), compared to the controls (not having an inner coating): 5 mg/cm² outer coating: 50% release was achieved within 530 min; 4 mg/cm² outer coating: 50% release within 415 min; 3 mg/cm² outer coating: 50% release within 275 min.

Further experiments were carried out using the following prednisolone-containing tablets: i) control tablets containing Eudragit® L 30D-55, 3, 4 and 5 mg/cm², respectively; ii) double-coated tablets comprising outer coating Eudragit® L 30D-55, 3, 4 and 5 mg/cm², respectively; inner coating of Eudragit® L 30D-55, 10% by weight adipic acid, pH 5.6. The tablets were subjected to a solution of 0.1 N HCl for 2 h and subsequently to a phosphate buffer pH 5.6. Table 5 shows the results of the dissolution of double coated tablets for 10% adipic acid formulation.

Table 5 shows the dissolution profiles of 10% adipic acid-containing Eudragit® L 30D-55 double coated prednisolone tablets in 0.1N HCl for 2 h and subsequent pH 5.6 phosphate buffer (all the formulations have the same outer coat: Eudragit®L30D-55, 5 mg/cm²).

| time [min] | Control: coating: Eudragit ®L30D-55 5 mg/cm² | Control: coating: Eudragit ®L30D-55 4 mg/cm² | Control: coating: Eudragit ®L30D-55 3 mg/cm² | outer coating: Eudragit ®L30D-55 5 mg/cm² inner coating: Eudragit ®L30D-55; 10% adipic acid, pH 5.6, 5 mg/cm² | outer coating: Eudragit ®L30D-55 4 mg/cm² inner coating: Eudragit ®L30D-55; 10% adipic acid, pH 5.6, 5 mg/cm² | outer coating: Eudragit ®L30D-55 3 mg/cm² inner coating: Eudragit ®L30D-55; 10% adipic acid, pH 5.6, 5 mg/cm² |
|---|---|---|---|---|---|---|
| 120 | 0.0 | 0.0 | 0.0 | 0.0 | 0.0 | 0.0 |
| 165 | 0.0 | 0.0 | 0.4 | 0.6 | 11.9 | 4.5 |
| 180 | 0.0 | 0.0 | 1.3 | 2.2 | 36.1 | 7.1 |
| 200 | 0.2 | 0.5 | 3.6 | 29.9 | 67.7 | 10.0 |

Example 3

Effects of the Degree of Neutralization of the Inner Coating Solution

In this experiment the effects of the degree of neutralisation of the inner coating solution on the drug release profiles was investigated. For this test double coated tablets with an inner coating of Eudragit® L30D-55 comprising 10% by weight citric acid is used. In detail: for this experiment the following prednisolone-containing tablets were used: i) control tablets containing Eudragit® L 30D-55, 5 mg/cm²; ii) double-coated tablets comprising outer coating Eudragit® L 30D-55, 5 mg/cm²; inner coating of Eudragit® L 30D-55, 10% by weight citric acid, pH 5.6, 5.8 and 6.0, respectively, 5 mg/cm². The tablets were subjected to a solution of 0.1 N HCl for 2 h and subsequently to a phosphate buffer pH 5.6.

The experiment shows a slight increase of drug release when the pH of inner coating solution was increased from pH 5.6 to pH 5.8. When neutralizing the inner coating solution to pH 6.0 the drug release rate was further significantly increased (see table 6). Here, the lag time of drug release in pH 5.6 phosphate buffer was reduced from 40 min to 5 min.

Table 6 shows the dissolution profiles of 10% citric acid-containing Eudragit® L 30D-55 double coated prednisolone tablets with different neutralisation values in 0.1N HCl for 2 h and subsequent pH 5.6 phosphate buffer (all the formulations have the same outer coat: Eudragit®L30D-55, 5 mg/cm²)

| time [min] | Control: Coating: Eudragit ®L30D-55 5 mg/cm² | outer coating: Eudragit ®L30D-55 inner coating: Eudragit ®L30D-55; 10% by weight citric acid, pH 5.6 | outer coating: Eudragit ®L30D-55 inner coating: Eudragit ®L30D-55; 10% by weight citric acid, pH 5.8 | outer coating: Eudragit ®L30D-55 inner coating: Eudragit ®L30D-55; 10% by weight citric acid, pH 6.0 |
|---|---|---|---|---|
| 120 | 0.0 | 0.0 | 0.0 | 0.0 |
| 135 | 0.0 | 0.0 | 0.0 | 9.9 |
| 160 | 0.0 | 2.8 | 12.9 | 57.4 |
| 170 | 0.0 | 12.7 | 24.8 | 78.2 |
| 190 | 0.0 | 52.1 | 60.3 | 92.4 |
| 375 | 10.0 | 106.3 | 96.0 | 94.9 |
| 535 | 50.0 | n.d. | n.d. | n.d. |

Example 4

Effects on the Drug Release Using Eudragit® L 100 as Inner Coat

For investigating the influence of the type of polymer on the drug release Eudragit® L 100 was used as inner coating solution which was neutralised to pH 6.2. For this experiment the following prednisolone-containing tablets were used: i) control tablets containing Eudragit® L 30D-55, 5 mg/cm²; ii) double-coated tablets comprising outer coating Eudragit® L 30D-55, 5 mg/cm²; inner coating of Eudragit® L100, 10% by weight citric acid, pH 6.2, 5 mg/cm². The tablets were subjected to a solution of 0.1 N HCl for 2 h and subsequently to a phosphate buffer pH 5.6.

As result it was observed that drug release from double coated tablets with Eudragit® L 100 and 10% by weight citric acid as inner coating showed very fast drug release profile, with only 5 min lag time (10% drug release within 145 min, 50% drug release within 170 min), which was much faster than control Eudragit® L 30D-55 coating (10% drug release within 370 min, 50% drug release within 530 min).

Further, different neutralisation values of Eudragit® L 100 as pH 6.2 and pH 6.8 were compared. For this experiment the following prednisolone-containing tablets were used: i) control tablets containing Eudragit® L 30D-55, 5 mg/cm²; ii) double-coated tablets comprising outer coating Eudragit® L 30D-55, 5 mg/cm²; inner coating of Eudragit® L100, 10% by weight citric acid, pH 6.2 and 6.8, respectively, 5 mg/cm²; iii) double-coated tablets comprising outer coating Eudragit® L 30D-55, 5 mg/cm²; inner coating of Eudragit® L100, 15% by weight adipic acid, pH 6.8, 5 mg/cm²; iv) double-coated tablets comprising outer coating Eudragit® L 30D-55, 5 mg/cm²; inner coating of Eudragit® L30D-55, 10% by weight citric acid, pH 5.6 and 6.0, respectively, 5 mg/cm². The tablets were subjected to a solution of 0.1 N HCl for 2 h and subsequently to a phosphate buffer pH 5.6.

Different neutralisation values of Eudragit® L 100 as pH 6.2 and pH 6.8 were compared and drug release profiles at these two neutralisation values showed no differences (Table 7). Comparing to the double coating formulation with Eudragit® L 30D-55 as inner coat at pH 6.0 neutralisation level, drug release from Eudragit® L 100 with 10% citric acid double coated tablets had the same lag time (5 min), but showed slightly slower slope of release profile. Inner coat formulation with Eudragit® L 100 and 15% adipic acid was also investigated, and showed very fast drug release, with 5 min lag time and release slope similar to Eudragit® L 30D-55, pH 6.0 formulation.

TABLE 7

Dissolution profiles of Eudragit ® L 30D-55, L100 double coated prednisolone tablets in 0.1N HCl for 2 h and subsequent pH 5.6 phosphate buffer (all the formulations have the same outer coat: Eudragit ® L 30D-55, 5 mg/cm²)

| time [min] | Control: coating: Eudragit ®L30D-55 5 mg/cm² | outer coating: Eudragit ®L30D-55 inner coating: Eudragit ®L100, 10% citric acid, pH 6.2 | outer coating: Eudragit ®L30D-55 inner coating: Eudragit ®L100, 10% citric acid, pH 6.8 | outer coating: Eudragit ®L30D-55 inner coating: Eudragit ®L30D-55; 10% citric acid, pH 6.0 | outer coating: Eudragit ®L30D-55 inner coating: Eudragit ®L30D-55; 10% citric acid, pH 5.6 | outer coating: Eudragit ®L30D-55 inner coating: Eudragit ®L100; 10% adipic acid, pH 6.8 |
|---|---|---|---|---|---|---|
| 120 | 0.0 | 0.3 | 0.0 | 0.0 | 0.0 | 0.0 |
| 135 | 0.0 | 3.9 | 4.2 | 9.9 | 0.0 | 8.3 |
| 150 | 0.0 | 18.3 | 19.1 | 36.0 | 0.5 | 30.6 |
| 170 | 0.0 | 49.7 | 55.2 | 78.2 | 12.7 | 67.7 |
| 190 | 0.0 | 83.1 | 81.1 | 92.4 | 52.1 | 88.2 |
| 375 | 10.0 | 96.1 | 94.5 | 94.9 | 106.8 | 92.6 |

Example 5

Acid Resistance Tests for Double Coated Prednisolone Tablets

In this experiment the acid resistance of double coated prednisolone tablets was studied. For this experiment the following prednisolone-containing tablets were used: i) control tablets containing Eudragit® L 30D-55, 5 mg/cm²; ii) double-coated tablets comprising outer coating Eudragit® L 30D-55, 5 mg/cm²; inner coating of Eudragit® L30D-55, 10% by weight adipic acid, pH 5.6, 5 mg/cm². The tablets were subjected to 0.1 N HCl solutions of different pH. As result is was shown that there is no drug release in 0.1 N HCl for 21 h, and also no drug release in HCl solution for 3 h having pH 2.0, 3.0 and 4.0, respectively. These results indicate that the double coating system has good acid resistance (data not shown).

Example 6

Comparison of Drug Release from Double Coated Prednisolone Tablets Comprising Either Citric Acid or Adipic Acid In this experiment the influence of the type of organic acid is investigated. For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$; inner coating of Eudragit® L30D-55, 10% by weight adipic acid or citric acid, respectively, pH 5.6, 5 mg/cm$^2$.

Table 8 shows the comparison of drug release from double coated and control coated prednisolone tablets at pH 5.6 phosphate buffer after 2 h in 0.1 N HCl. All the inner coat of the double coated formulations were neutralized to pH 5.6.

In particular the drug released from 10% citric acid and 10% adipic acid double coated tablets in pH 5.5, 5.6 and 5.8 buffer were tested (table 8 only shows the double coated tablets in pH 5.6 buffer). In all of the test pH values, double coated tablets containing an organic acid (either citric acid or adipic acid) showed faster drug release than control coated tablets. In all of these three pH values, 10% citric acid formulation showed faster drug release rates than 10% adipic acid formulation.

TABLE 8

Drug release profiles of Eudragit ® L 30D-55 double coated and control coated prednisolone tablets in 0.1N HCl for 2 h and subsequent pH 5.6 phosphate buffer: all the double coated formulations have the same outer coat: Eudragit ®L30D-55, 5 mg/cm$^2$

| time [min] | Control: coating: Eudragit ®L30D-55 5 mg/cm$^2$ | outer coating: Eudragit ®L30D-55 inner coating: Eudragit ®L30D-55, 10% adipic acid, pH 5.6 | outer coating: Eudragit ®L30D-55 inner coating: Eudragit ®L30D-55, 10% citric acid, pH 5.6 |
|---|---|---|---|
| 120 | 0.0 | 0.0 | 0.0 |
| 155 | 0.0 | 0.0 | 1.0 |
| 170 | 0.0 | 1.0 | 12.7 |
| 190 | 0.0 | 6.7 | 52.1 |
| 200 | 0.2 | 29.9 | 71.9 |
| 235 | 1.0 | 93.3 | 102.8 |
| 375 | 10.0 | 103.0 | 106.8 |

Example 7

Drug Release Studies with Theophylline Pellets; Comparison

The present example shows the effects of double coating on theophylline pellets. For this experiment the following theophylline-containing pellets were used: i) control pellets containing Eudragit® L30D-55, 5 mg/cm$^2$, ii) double coated pellets comprising outer coating Eudragit® L30D-55, 5 mg/cm$^2$, inner coating of Eudragit® L30D-55, 10% citric acid, pH 5.6.

In this experiment the acid resistance of double coated theophylline pellets was tested. It was shown that the use of a different active ingredient, theophylline, that there was no drug release from double coated pellets in 0.1 N HCl for 2 h, which indicates that the double coating formulation has good acid resistance.

Further tests refer to the drug release from double coated and control coated theophylline pellets at pH 5.0 and 5.5, phosphate buffer after 2 h in 0.1 N HCl. There was very slow drug release from control coated pellets at pH 5.5, and no drug release from these pellets at pH 5.0. However, for double coated pellets, drug releases already started at pH 5.0 and showed fast and complete drug release at pH 5.5.

Example 8

Coating Dissolution Process for Double Coated, HPMC Inner coating ("subcoated") and control coated prednisolone pellets For this experiment the following prednisolone-containing pellets were used: i) control pellets containing Eudragit® L 30D-55, 5 mg/cm$^2$; ii) double-coated pellets comprising outer coating Eudragit® L 30D-55, 5 mg/cm$^2$, inner coating of Eudragit® L 30D-55, 15% by weight adipic acid, pH 5.6, 5 mg/cm$^2$; iii) HPMC subcoated pellets containing outer coating Eudragit® L 30D-55, 5 mg/cm$^2$, inner coating HPMC pH 7.0, 3 mg/cm$^2$.

As result is was observed that there were no drug release from both 15% adipic acid double-coated pellets and control Eudragit® L 30D-55 coated pellets in 0.1 M HCl for 2 h. However, in subsequent pH 5.5 buffer, prednisolone release from 15% adipic acid double-coated pellets was much faster than control coated pellets, with lag time 40 min and 105 min respectively.

Double-coated pellets with HPMC E5 (hydroxypropyl methylcellulose) 3 mg/cm$^2$ as a subcoat (inner coating) were also investigated. The lag time for drug release from HPMC-subcoated pellets was reduced to 90 min, 15 min faster than the control coated pellets (data not shown).

Example 9

Drug Release of Tablets Comprising Inner Coating with Only Neutralization without Organic Acid For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55 (5 mg/cm$^2$), 10% citric acid, pH 5.6 or 6.0, respectively; iii) double-coated pellets comprising outer coating Eudragit® L 30D-55, 5 mg/cm$^2$, inner coating of Eudragit® L 30D-55 (5 mg/cm$^2$), pH 5.8 or 6.0, respectively. If neutralizing the inner coat to pH 5.8 and pH 6.0 without adding organic acid, the double coated tablets still showed faster drug release than the control. However the inventive formulations with 10% citric acid showed even faster drug release at comparable pH values of 5.8 or 6.0, respectively (table 9). These results clearly show that without the addition of organic acids the mere higher neutralization degree of the inner coating compared to the outer coating a dramatic increase in the drug release rate is achieved, however the drug release rate is not as good as for formulations which include organic acids in the inner coating.

TABLE 9

Dissolution profiles of Eudragit ® L 30D-55 double coated prednisolone tablets with or without citric acid in 0.1N HCl for 2 h and subsequent pH 5.6 phosphate buffer (all the formulations have the same outer coat: Eudragit ®L30D-55, 5 mg/cm$^2$)

| time [min] | Control: coating: Eudragit ®L30D-55 5 mg/cm$^2$ | outer coating: Eudragit ®L30D-55 inner coating: Eudragit ®L30D-55, 10% citric acid, pH 5.8 | outer coating: Eudragit ®L30D-55 inner coating: Eudragit ®L30D-55, 10% citric acid, pH 6.0 | outer coating: Eudragit ®L30D-55 inner coating: Eudragit ®L30D-55, pH 5.8 (no addition of acid) | outer coating: Eudragit ®L30D-55 inner coating: Eudragit ®L30D-55, pH 6.0 (no addition of acid) |
|---|---|---|---|---|---|
| 120 | 0.0 | 0.0 | 0.0 | 0.0 | 0.0 |
| 125 | 0.0 | 0.0 | 0.4 | 0.0 | 0.0 |
| 140 | 0.0 | 1.4 | 17.4 | 0.0 | 1.7 |
| 155 | 0.0 | 8.7 | 46.5 | 0.5 | 11.6 |
| 170 | 0.0 | 24.9 | 78.3 | 5.1 | 30.2 |
| 180 | 0.0 | 43.1 | 89.1 | 14.9 | 45.4 |
| 190 | 0.0 | 60.4 | 92.4 | 26.6 | 59.4 |
| 210 | 0.2 | 83.3 | 93.7 | 53.6 | 80.5 |
| 375 | 10.0 | 96.0 | 94.9 | 95.1 | 90.4 |

Example 10

Drug Release of Double Coated Tablets Comprising Inner Coating with Organic Acid but without Neutralization For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 20% citric acid, pH 5.6, 5 mg/cm$^2$; iii) double-coated tablets comprising outer coating Eudragit® L 30D-55, 5 mg/cm$^2$, inner coating of Eudragit® L 30D-55, 20% by weight citric acid, non-neutralized, 5 mg/cm$^2$. Double coated tablets with inner coat having 20% citric acid, but non-neutralized, showed no drug release in pH 5.6 phosphate buffer for 12 h (table 10 shows up to 6 hours). Assumingly, the acidity of citric acid in the inner coat decreased the microenvironment pH of Eudragit® L 30D-55 outer coat, thus decreased the coat dissolution speed.

Example 11

Drug Release of Double Coated Tablets Comprising HPMC as Inner Coating

For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 20% citric acid, pH 5.6, 5 mg/cm$^2$; iii) double-coated tablets comprising outer coating Eudragit® L 30D-55, 5 mg/cm$^2$, inner coating of HPMC E-5, using 1, 3 and 5 mg/cm$^2$, respectively, pH 7.0.

The tablets were subjected to 0.1N HCl for 2 h and subsequently to pH 5.6 phosphate buffer. The dissolution rates for 1 mg/cm$^2$ and 3 mg/cm$^2$ HPMC E5 inner coated tablets were faster than control coat (data not shown). The fastest drug release was found with HPMC E5 inner coat amount at 3 mg/cm$^2$, but still slower than Eudragit® L 30D-55, 20% citric acid, pH 5.6 inner coated formulation.

Further experiments were carried out with the following prednisolone-containing tablets: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 10% citric acid, pH 5.6 and 6.0, respectively, 5 mg/cm$^2$; iii) double-coated tablets comprising outer coating Eudragit® L 30D-55, 5 mg/cm$^2$, inner coating of HPMC E 5, 5 mg/cm$^2$, with either

TABLE 10

Dissolution profiles of Eudragit ® L 30D-55 double coated prednisolone tablets with or without neutralization in 0.1N HCl for 2 h and subsequent pH 5.6 phosphate buffer (all the formulations have the same outer coat: Eudragit ®L30D-55, 5 mg/cm$^2$)

| time [min] | Control: coating: Eudragit ®L30D-55 5 mg/cm$^2$ | outer coating: Eudragit ®L30D-55 inner coating: Eudragit ®L30D-55, 20% citric acid, pH 5.6 | outer coating: Eudragit ®L30D-55 inner coating: Eudragit ®L30D-55; 20% citric acid, non-neutralized |
|---|---|---|---|
| 120 | 0.0 | 0.0 | 0.0 |
| 165 | 0.0 | 9.0 | 0.2 |
| 170 | 0.0 | 13.2 | 0.1 |
| 175 | 0.0 | 31.4 | 0.0 |
| 185 | 0.0 | 77.1 | 0.0 |
| 195 | 0.0 | 87.0 | 1.4 |
| 300 | 5.2 | 97.7 | 0.5 |
| 375 | 10.0 | 99.3 | 0.7 | a) 10% citric acid which was completely neutralized or b) 10% Na citrate or c) 10% NaCl, respectively, each having pH 7.0.

As summarized in table 11, the tablets comprising 10% NaCl, Na citrate and citric acid (with equal Mole of NaOH to completely neutralized) included in the HPMC E5 inner coat formulation showed fast drug release profiles (table 11). The HPMC E5 with 10% salt formulations still showed slower drug release comparing to Eudragit® L 30D-55, 10% citric acid, pH 6.0 inner coat formulation.

5.6, 5 mg/cm$^2$; iii) HP-55 coated tablets, 5 mg/cm$^2$; iv) double-coated tablets comprising outer coating HP-55, 5 mg/cm$^2$, inner coating of Eudragit® L 30D-55, 10% citric acid, pH 5.6, 5 mg/cm$^2$. The tablets were subjected to 0.1N HCl for 2 h and subsequently to pH 5.6 phosphate buffer.

Enteric coated prednisolone tablets with HP-55 (hydroxypropyl methylcellulose phthalate, which is an anionic polymer) as coating polymer showed much faster drug release than Eudragit® L 30D-55 with same amount of polymer

TABLE 11

Dissolution profiles of Eudragit ® L 30D-55 double coated prednisolone tablets with HPMC E5 as inner coat in 0.1N HCl for 2 h and subsequent pH 5.6 phosphate buffer (all the formulations have the same outer coat: Eudragit ®L30D-55, 5 mg/cm$^2$)

| time [min] | Control: Eudragit ®L30D-55 enteric coating; no inner coating | outer coating: Eudragit ®L30D-55 inner coating: HPMC; 10% citric acid, completely neutralized with NaOH; | outer coating: Eudragit ®L30D-55 inner coating: HPMC; 10% Na citrate, without neutralization | outer coating: Eudragit ®L30D-55 inner coating: HPMC; 10% NaCl, without neutralization | outer coating: Eudragit ®L30D-55 inner coating: Eudragit ®L30D-55, 10% citric acid pH 5.6 | outer coating: Eudragit ®L30D-55 inner coating: Eudragit ®L30D-55; 10% citric acid, pH 6.0 |
|---|---|---|---|---|---|---|
| 120 | 0.0 | 0.0 | 0.0 | 0.0 | 0.0 | 0.0 |
| 135 | 0.0 | 0.0 | 0.0 | 0.0 | 0.0 | 9.9 |
| 145 | 0.0 | 0.2 | 0.1 | 0.0 | 0.3 | 25.8 |
| 155 | 0.0 | 0.3 | 0.6 | 0.0 | 1.0 | 46.4 |
| 170 | 0.0 | 5.7 | 7.5 | 0.0 | 12.7 | 78.2 |
| 175 | 0.0 | 10.0 | 10.1 | 2.2 | 22.6 | 85.1 |
| 185 | 0.0 | 22.3 | 18.4 | 14.1 | 42.4 | 91.3 |
| 195 | 0.0 | 37.7 | 29.5 | 33.4 | 62.8 | 92.9 |
| 200 | 0.2 | 48.3 | 34.5 | 45.0 | 71.9 | 93.2 |
| 215 | 0.3 | 75.1 | 52.8 | 71.6 | 90.4 | 93.4 |

Example 12

Drug Release of Double Coated Tablets Comprising HP-55 (Hydroxypropyl Methylcellulose Phthalate) as Outer Coating For this experiment the following prednisolone-containing tablets were used: i) control tablets containing Eudragit® L 30D-55, 5 mg/cm$^2$; ii) double-coated tablets comprising outer coating Eudragit® L 30D-55, 5 mg/cm$^2$, inner coating of Eudragit® L 30D-55, 10% citric acid, pH applied (5 mg/cm$^2$). There was no drug release from HP-55 coated tablets in 0.1 N HCl for 2 h. In subsequent pH 5.6 phosphate buffer, there was almost no drug release lag time for HP-55 coating. The drug release profiles for HP-55 coating showed two phases in pH 5.6 phosphate buffer. Drug release was slow in the first 20 min, and became very fast after that. HP-55 outer coating with Eudragit® L 30D-55, 10% citric acid, pH 5.6 formulation as inner coat showed further improvement of drug release. These results are summarized in table 12.

TABLE 12

Comparison of drug release from Eudragit ® L 30D-55 coating and HP-55 coating in 0.1N HCl for 2 h and subsequent pH 5.6 phosphate buffer

| time [min] | Control: Eudragit ®L30D-55 enteric coating; no inner coating | outer coating: Eudragit ®L30D-55 inner coating: Eudragit ®L30D-55; 10% citric acid, pH 5.6 | HP-55 coated no inner coating | outer coating: HP-55 inner coating: Eudragit ®L30D-55; 10% citric acid, pH 5.6 |
|---|---|---|---|---|
| 120 | 0.0 | 0.0 | 0.0 | 0.0 |
| 135 | 0.0 | 0.0 | 2.2 | 5.6 |
| 145 | 0.0 | 0.3 | 4.0 | 10.6 |
| 165 | 0.0 | 7.1 | 10.5 | 36.0 |
| 180 | 0.0 | 32.9 | 28.1 | 57.8 |
| 175 | 0.0 | 22.6 | 20.7 | 50.4 |
| 180 | 0.0 | 32.9 | 28.1 | 57.8 |
| 190 | 0.0 | 52.1 | 42.7 | 70.1 |

Example 13

Drug Release of Double Coated Tablets Comprising 10% Citric Acid, 10% Na Citrate and 20% NaCl, Respectively as Inner Coating For this experiment the following prednisolone-containing tablets were used: i) control tablets containing Eudragit® L 30D-55, 5 mg/cm²; ii) double-coated tablets comprising outer coating Eudragit® L 30D-55, 5 mg/cm², inner coating of Eudragit® L 30D-55, 10% citric acid, pH 5.6, 5 mg/cm²; iii) double-coated tablets comprising outer coating Eudragit® L 30D-55, 5 mg/cm², inner coating of Eudragit® L 30D-55, 10% citric acid, pH 6.0, 5 mg/cm², iv) double-coated tablets comprising outer coating Eudragit® L 30D-55, 5 mg/cm², inner coating of Eudragit® L 30D-55, 10% Na citrate, pH 6.0, 5 mg/cm²; v) double-coated tablets comprising outer coating Eudragit® L 30D-55, 5 mg/cm², inner coating of Eudragit® L 30D-55, 20% by weight NaCl, pH 5.6, 5 mg/cm². The tablets were subjected to 0.1N HCl for 2 h and subsequently to pH 5.6 phosphate buffer.

Table 13 shows the drug release profile of double coated prednisolone tablets with 10% by weight Na citrate in the inner coat and neutralized to pH 6.0. Compared to the 10% citric acid formulation (also neutralized to pH 6.0, drug release from the 10% Na citrate formulation was slower.

The double coated tablet having an inner coat formulation with 20% NaCl and also neutralized to pH 5.6 showed a drug release which was similar to the 10% citric acid pH 5.6 formulation (table 13).

It was not possible to coat with NaCl-containing non-neutralized Eudragit® L 30D-55 formulation. Eudragit® L 30D-55 dispersion changed to semi-solid after adding NaCl into the dispersion. The sendimented particles redissolved until adding 1 M NaOH and neutralized to pH 5.6.

TABLE 13 dissolution test of Eudragit ® L30D-55 double coated prednisolone tablets in 0.1N HCl for 2 h and subsequent pH 5.6 phosphate buffer (all formulations have the same outer coat: Eudragit ®L30D-55, 5 mg/cm²).

| Time [min] | Control: Eudragit ®L30D-55 enteric coating; no inner coating | outer coating: Eudragit ®L30D-55 inner coating: Eudragit ®L30D-55; 10% citric acid, pH 5.6 | outer coating: Eudragit ®L30D-55 inner coating: Eudragit ®L30D-55; 10% citric acid, pH 6.0 | outer coating: Eudragit ®L30D-55 inner coating: Eudragit ®L30D-55; 10% Na citrate, pH 6.0 | outer coating: Eudragit ®L30D-55 inner coating: Eudragit ®30D-55, 20% NaCl, pH 5.6 |
|---|---|---|---|---|---|
| 120 | 0.0 | 0.0 | 0.0 | 0.0 | 0.0 |
| 135 | 0.0 | 0.0 | 9.9 | 0.5 | 0.0 |
| 150 | 0.0 | 0.5 | 36.0 | 5.6 | 0.0 |
| 160 | 0.0 | 2.8 | 57.4 | 16.1 | 0.2 |
| 170 | 0.0 | 12.7 | 78.2 | 34.0 | 11.6 |
| 180 | 0.0 | 32.9 | 89.1 | 53.6 | 27.2 |
| 190 | 0.0 | 52.1 | 92.4 | 72.5 | 43.2 |
| 375 | 10.0 | 106.8 | 94.9 | n.d. | 94.1 |

The invention claimed is:

1. A solid dosage form comprising
an inner coating located between a core containing a pharmaceutically active ingredient and an outer enteric coating;
wherein said inner coating comprises a partially neutralized anionic polymeric material, and at least a carboxylic acid having 2 to 16 carbon atoms, the salts thereof or mixtures of said acid and its salt;
wherein said outer coating comprises an anionic polymeric material which is less neutralized than the material of the inner coating or not at all neutralized.

2. The solid dosage form according to claim 1, wherein the difference in the neutralization between the inner coating and the outer coating is at least 5 percentage points.

3. The solid dosage form according to claim 1, wherein the degree of neutralization of anionic groups of the outer coating is at most 10 percent.

4. The solid dosage form according to claim 1, wherein the anionic polymeric material of the inner coating and the outer coating, respectively, is independently selected from the group consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate, and shellac.

5. The solid dosage form according to claim 1,
wherein the inner coating is made of a partially neutralized anionic (meth)acrylate copolymer consisting of free-radical polymerized units of 25 to 95% by weight $C_1$- to $C_4$-alkyl esters of acrylic or methacrylic acid and 5 to 75% by weight (meth)acrylate monomers having an anionic group, wherein 1 to 80% of the contained anionic groups are neutralized by an alkaline agent;
and wherein the outer coating is made of an anionic (meth)acrylate copolymer consisting of free-radical polymerized units of 25 to 95% by weight $C_1$- to $C_4$-alkyl esters of acrylic or methacrylic acid and 5 to 75% by weight (meth)acrylate monomers having an anionic group.

6. The solid dosage form according to claim 1, wherein the salt is an alkali metal salt, an alkaline earth metal salt, an ammonium salt or a soluble metal salt.

7. The solid dosage form according to claim 1, wherein the carboxylic acid having 2 to 16 carbon atoms comprises 1, 2 or 3 carboxyl groups.

8. The solid dosage form according to claim 1, wherein the carboxylic acid is selected from the group consisting of sorbic acid, benzoic acid, fumaric acid, adipic acid, citric acid, succinic acid, glutaric acid, malic acid, tartaric acid, acetic acid, glycolic acid, malonic acid, propanoic acid, glyceric acid, trans-crotonic acid, itaconic acid, mesaconic acid, trimethylacetic acid, isocitric acid, hexanoic acid, 4-methylpentanoic acid, gallic acid, terephthalic acid, phenylacetic acid, mandelic acid, alpha-phenylpropanoic acid, beta-phenylpropanoic acid, lauric acid, caprylic acid, caprinic acid, myristic acid and mixtures thereof, the salts thereof and mixtures of said acid and its salt.

9. The solid dosage form according to claim 1, wherein the carboxylic acid is adipic acid or citric acid.

10. The solid dosage form according to claim 1. wherein each of the inner and the outer coatings contain 2 to 10 mg/cm$^2$ polymer weight gain.

11. The solid dosage form according to claim 1, wherein the relation between the inner and the outer coating is 10:90 to 90:10 by weight of dry polymer.

* * * * *